United States Patent [19]

Stone et al.

[11] Patent Number: 5,732,821
[45] Date of Patent: Mar. 31, 1998

[54] SYSTEM FOR STERILIZING MEDICAL DEVICES

[75] Inventors: Kevin T. Stone, Warsaw; Jeffrey D. Gordon, Claypool; Barry F. Hecker, Pierceton, all of Ind.; William H. Fox, III, Jacksonville, Fla.

[73] Assignee: Biomet, Inc., Warsaw, Ind.

[21] Appl. No.: 535,531

[22] Filed: Sep. 28, 1995

[51] Int. Cl.[6] ............................................. A61B 19/02
[52] U.S. Cl. .................................. 206/370; 206/439
[58] Field of Search ....................... 220/23.83, 23.4; 206/370, 369, 363, 438, 439

[56] References Cited

U.S. PATENT DOCUMENTS

| | | |
|---|---|---|
| D. 225,468 | 12/1972 | Burke et al. . |
| D. 226,266 | 2/1973 | Rem et al. . |
| D. 276,462 | 11/1984 | Villarreal . |
| D. 288,605 | 3/1987 | Asenbauer . |
| D. 288,846 | 3/1987 | Leonard . |
| 354,799 | 12/1886 | McConahy . |
| 670,446 | 3/1901 | Fletcher et al. . |
| 1,222,844 | 4/1917 | Caldemeyer . |
| 1,492,113 | 4/1924 | Welsh . |
| 1,521,289 | 12/1924 | Guttman . |
| 1,736,651 | 11/1929 | Glaenzer . |
| 4,227,758 | 10/1980 | Clare .......................... 220/23.4 X |
| 4,501,363 | 2/1985 | Isbey, Jr. . |
| 4,544,300 | 10/1985 | Lew et al. . |
| 4,595,102 | 6/1986 | Cianci et al. . |
| 4,652,170 | 3/1987 | Lew . |
| 4,728,234 | 3/1988 | Reynard ...................... 220/23.4 X |
| 4,785,936 | 11/1988 | Shpigelman . |
| 4,807,776 | 2/1989 | Cortopassi ................... 220/23.83 |
| 4,817,809 | 4/1989 | Rozmestor ................... 220/23.4 |
| 4,863,451 | 9/1989 | Marder . |
| 4,880,122 | 11/1989 | Martindell . |
| 4,946,058 | 8/1990 | Stumm ........................ 220/23.83 |
| 5,078,530 | 1/1992 | Kim . |
| 5,181,297 | 1/1993 | Andrews, Jr. et al. ...... 220/23.4 X |
| 5,305,879 | 4/1994 | Noschese . |
| 5,305,902 | 4/1994 | Vozick ........................ 220/23.4 |
| 5,339,976 | 8/1994 | Thornton ..................... 220/23.4 |
| 5,386,922 | 2/1995 | Jordan ......................... 220/23.83 |
| 5,394,983 | 3/1995 | Latulippe et al. . |
| 5,445,641 | 8/1995 | Frigg et al. . |

*Primary Examiner*—Jacob K. Ackun
*Attorney, Agent, or Firm*—Harness, Dickey & Pierce, P.L.C.

[57] ABSTRACT

A system for storing and sterilizing orthopedic devices in a series of cases that may be attached together to provide a custom type container for a particular end user. The containers have modular compartments for housing the orthopedic devices. The containers may be shipped with the orthopedic devices in a sterilized environment as well as be resterilized in an autoclave for future use. A method of use and inventory control is also disclosed wherein a container using a generic marking system is used on the lid for the container. An inventory control sheet is used to record the part number and manufacturing lot number of the components housed in the compartments. The sheet corresponds to the generic marking system. A more accurate accounting of the inventory is achieved.

22 Claims, 14 Drawing Sheets

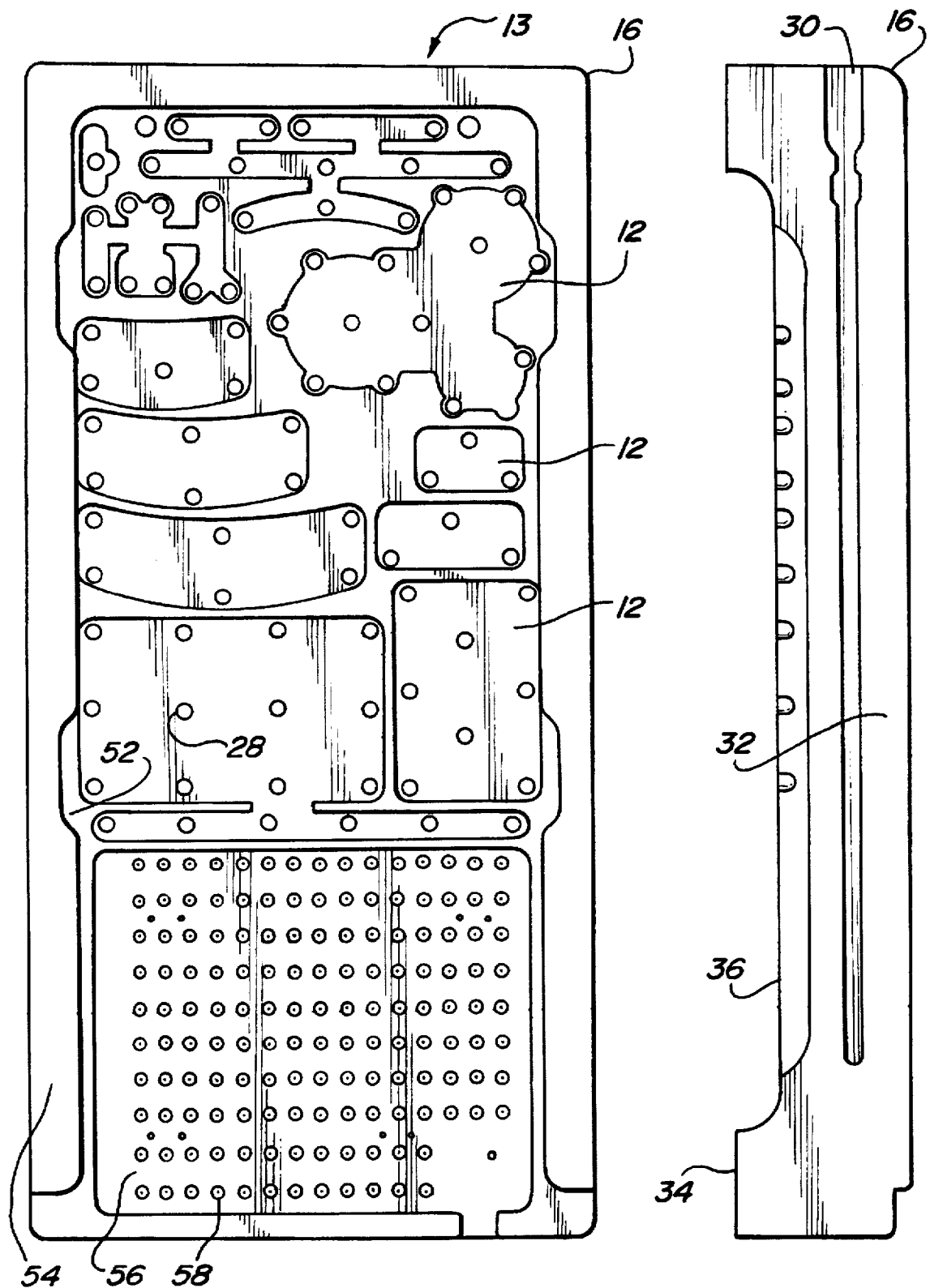

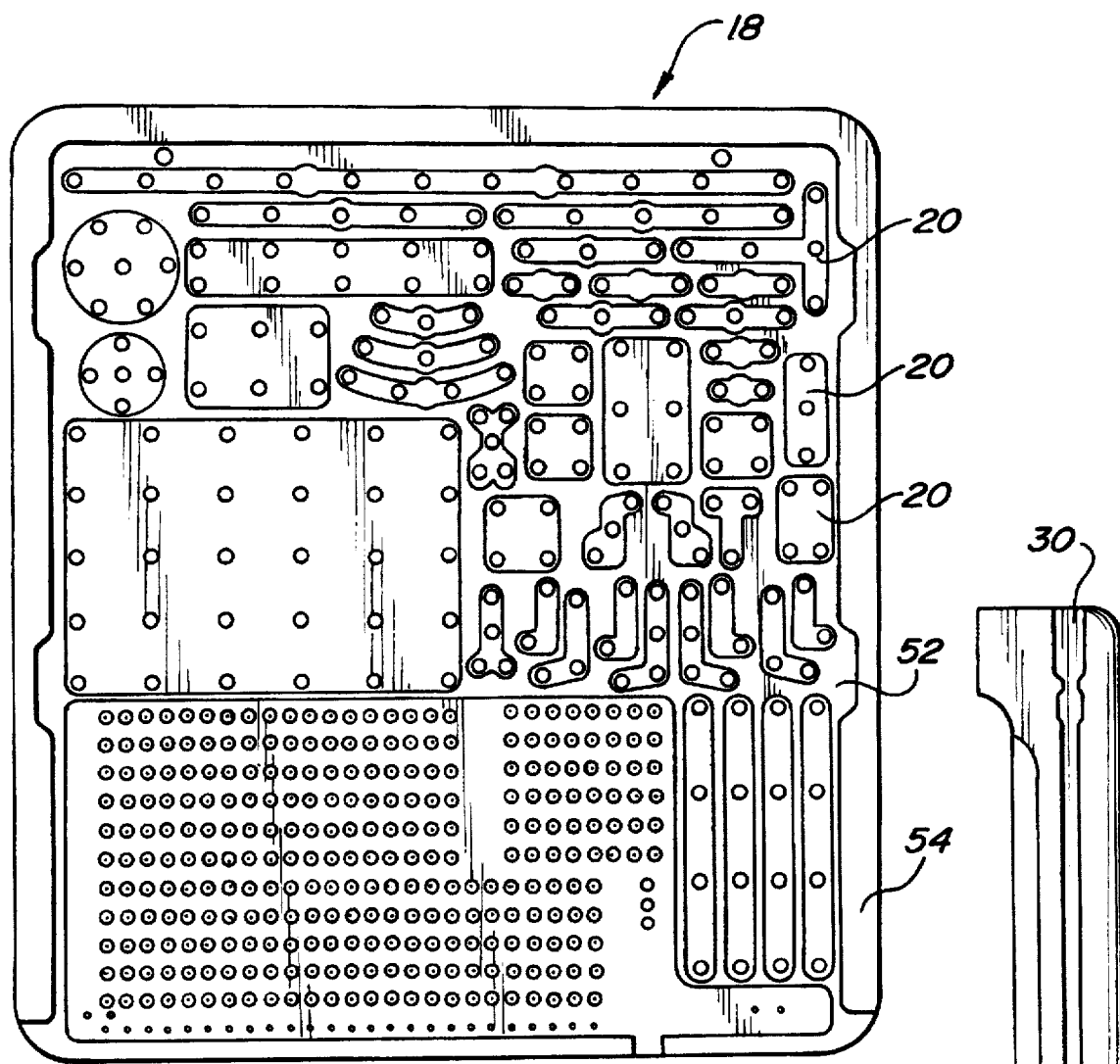
*Fig-3A*
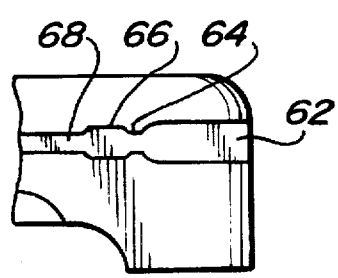
*Fig-3F*
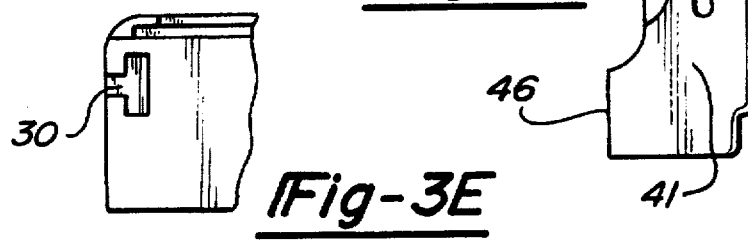
*Fig-3E*
*Fig-3B*

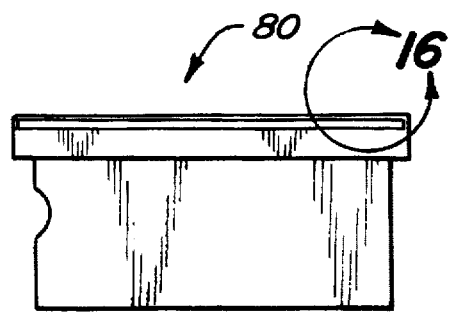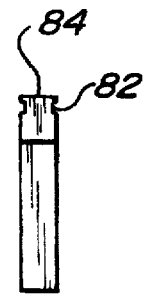
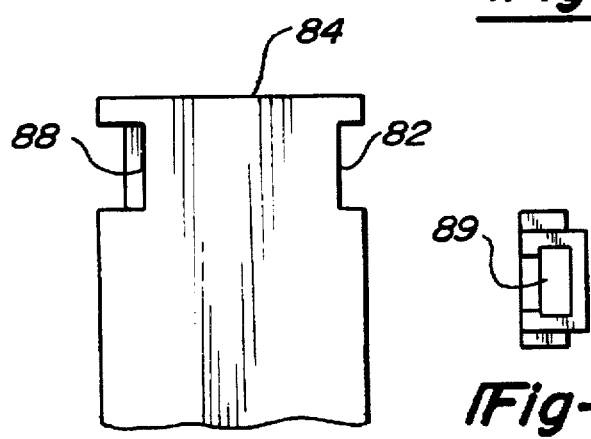
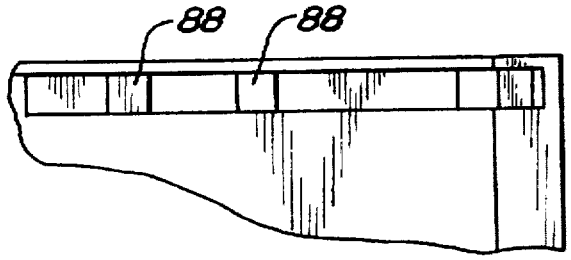
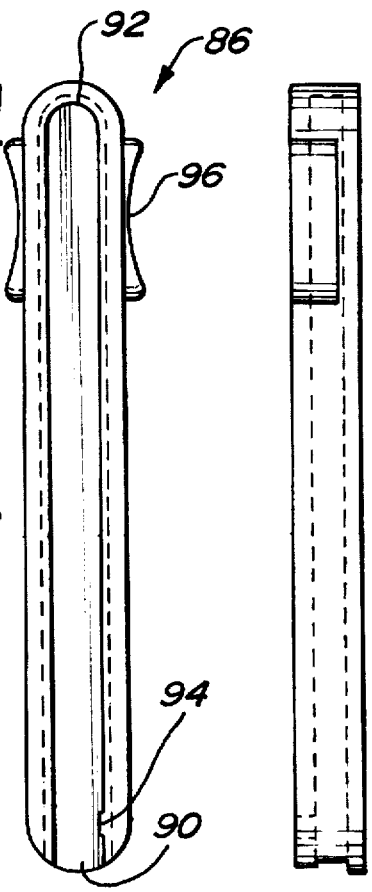

IFig-21

| 01-7066 STRAIGHT PLATE. REGULAR 16 HOLE 1.5 SYSTEM | | | | | |
|---|---|---|---|---|---|
| 1 QTY. PRICE | 2 QTY. PRICE | ... | 3 QTY. PRICE |
| 4 QTY. PRICE | 5 QTY. PRICE | ... | 6 QTY. PRICE |
| 7 QTY. PRICE | 8 QTY. PRICE | ... | 9 QTY. PRICE |
| 10 QTY. PRICE | QTY. PRICE | ... | QTY. PRICE |
| QTY. PRICE | QTY. PRICE | ... | QTY. PRICE |

...

| QTY. PRICE | QTY. PRICE | ... | QTY. PRICE |

| 01-7202 CENTER-DRIVE SCREW. 1.5X2.5mm 1.5 SYSTEM | QTY. PRICE | 01-7205 CENTER-DRIVE SCREW. 1.5X15mm 1.5 SYSTEM | QTY. PRICE |
|---|---|---|---|
| 01-7203 CENTER-DRIVE SCREW. 1.5X3.5mm 1.5 SYSTEM | QTY. PRICE | 01-7223 CENTER-DRIVE SCREW. 1.8X3.5mm 1.5 SYSTEM | QTY. PRICE |
| 01-7204 CENTER-DRIVE SCREW. 1.5X4mm 1.5 SYSTEM | QTY. PRICE | 01-7225 CENTER-DRIVE SCREW. 1.5X5mm 1.5 SYSTEM | QTY. PRICE |
| 01-7206 CENTER-DRIVE SCREW. 1.5X6mm 1.5 SYSTEM | QTY. PRICE | 01-7227 CENTER-DRIVE SCREW. 1.5X7mm 1.5 SYSTEM | QTY. PRICE |

SYSTEM FOR STERILIZING MEDICAL DEVICES

BACKGROUND OF THE INVENTION

The invention relates generally to containers for storage and sterilization of maxillofacial medical implants and instruments and, more specifically, to a series of containers that may be attached together to form a customized set of maxillofacial medical implants and instruments for a particular end user.

During various types of surgical procedures, it is often necessary to secure adjacent bone portions together. In certain neurosurgical procedures, for example, a cranial bone flap is first formed on the skull and then removed so that a surgeon can access the portions of the brain that are of concern. Such a cranial bone flap may typically be formed by drilling several burr holes through the cranial vault. After the burr holes have been drilled, osteotomies are made by a saw in the skull which connect the burr holes. The saw may typically have a guide nose which serves to avoid injuries to the dura mater. The bone flap is then removed so as to provide access to the brain. Once the procedures performed on the brain have been completed, the bone flap is reattached to the skull.

A variety of devices are commercially available which are used for reattaching and/or securing adjacent bone portions together. For example, U.S. Pat. No. 5,210,737 discloses a device having a plurality of slots which extend radially from the center of the device. The slots are indicated as being used for forming a plurality of vanes in the device, while vanes are secured to adjacent bone portions by screws. Other types of plate and screw systems are also used for a variety of maxillofacial procedures. Generally, these types of fixation devices are available in many different shapes and sizes.

As will be appreciated by those skilled in the art, orthopedic devices must generally be sterilized prior to implantation. Currently, sterilization containers used for sterilizing and housing medical implants and instruments are well known. Because maxillofacial implants and instruments come in many sizes, it may be necessary to provide more than one container to hold all of the devices. For example, the containers may come in different sizes and hold various components such as a 1.0 mm plate and screw system or a 1.5 mm plate and screw system. If only a few items from a large container are desired, the entire container must be sterilized and placed in the operating room during the surgery. The containers are scattered about the sterile field or may actually be stacked on top of each other making location of a desired instrument or implant difficult and time consuming.

In addition, because of the individual preferences and needs of the surgeon in terms of the specific devices which the surgeon uses, each surgeon typically has a customized sterilization container made which is able to store the specific devices which the surgeon uses most frequently. However, not only is this relatively expensive in terms of manufacturing such a customized sterilized container, but the use of such individualized sterilization containers for each surgeon typically increased the inventory costs associated with such orthopedic devices. This is because each surgeon has to maintain a usable inventory of each of the orthopedic devices in each of the individualized sterilization containers.

Manufacturers of orthopedic implants often maintain traceability of their inventory for various reasons. In addition, hospitals also desire to maintain inventory control in order to properly bill patients for only the components used on each case.

Current practice is to ship implants in a non-sterile package and hand load them into a sterilization tray to be sterilized. The packaging that initially housed the implant normally has the manufacturing part and lot numbers on it. The packaging is then separated from the implant making inventory and lot control difficult if not impossible. For example, if a tray holds 50 implantable bone screws and the previous surgery used 27 screws, then more screws will be added to the tray for the next case. The next set of screws may not be from the same manufacturing lot as the first group. The screws will not necessarily be removed from the case on a first-in-first-out basis. This continues for many surgical procedures until it is impossible to determine the manufacturing lot number for each screw in the sterilization tray.

One method of inventory control is to provide a sterilization case with a lid. The lid has indicia in the form of a part number corresponding to the components in the different compartments inside the container. The above method works well until a change is made in the system and the lid no longer corresponds to the components inside. In either situation, a new lid is then required for the sterilization case.

SUMMARY OF THE INVENTION

The present invention overcomes the problems and disadvantages of the above-described prior art sterilization and housing containers by providing an improved system for housing and sterilizing medical devices for surgery. The system includes a first container having multiple compartments. The first container may be detachably mounted to a second container having multiple compartments thus combining a first set of orthopedic devices with a second set of orthopedic devices. In effect, a customized sterilization and housing container may be put together by the end user.

Another embodiment of the invention is to provide a container with apertures that allow for modular compartments to be added into the container by fitting the compartments into the apertures.

A further embodiment is a method whereby inventory may be more accurately controlled. The method used is to first provide an initial inventory to be housed in the container. The container is provided with a lid having generic marking on each compartment such as A, B, C . . . or 1, 2, 3 . . . . An inventory control sheet is provided having a layout that corresponds to the layout of the container with a similar designation as the generic marking. The orthopedic devices that are housed inside each compartment are each designated by a part number and a manufacturing lot number by the manufacturer. The part numbers and lot numbers are written on the inventory control sheet as well as the quantity. When a part is used, it can be recorded on the inventory control sheet by part number and manufacturing lot number to be used for patient billing.

One advantage of the current invention is to provide a modular set of storage and sterilization containers that may be "customized" for a particular end user.

A further advantage of the current invention is to provide a structure to house screws that helps maintain inventory control.

Still another advantage of the current invention is to allow for shipment of screws and implants in a sterile packaged compartment that may be inserted into a storage/sterilization container in the operating room.

Yet another advantage of the current invention is to provide a method to maintain inventory control with the use of a separate inventory control sheet that corresponds to the sterilization container.

BRIEF DESCRIPTION OF THE DRAWINGS

Various advantages of the present invention will become apparent to one skilled in the art upon reading the following specification and reference to the following drawings in which:

FIG. 2a is a top elevational view of the first sterilization container of the present invention;

FIG. 2b is a side elevational view of the first sterilization container of the present invention;

FIG. 3a is a top elevational view of a second sterilization container of the present invention;

FIG. 3b is a side elevational view of the second sterilization container of the present invention;

FIG. 3e is an enlarged elevational view of the T-slot used with the sterilization containers of the present invention;

FIG. 3f is a side elevational view of the T-slot used with the sterilization containers of the present invention;

FIG. 14 is a front, end and top elevational view of a modular compartment of the present invention;

FIG. 15 is a detail view of the slot of the modular compartment of the present invention;

FIG. 16 is a detail view of the modular compartment of the present invention;

FIG. 17A–17C is a three-sided view of the lid for the modular compartment of the present invention;

FIG. 21 is a view of the reverse side of the inventory control sheet of the present invention.

DESCRIPTION OF THE PREFERRED EMBODIMENT

The following discussion of the preferred embodiments of the present invention is merely exemplary in nature. Accordingly, the discussion is in no way intended to limit the scope of the invention, the application of the invention, or the use of the invention.

Figure 1:
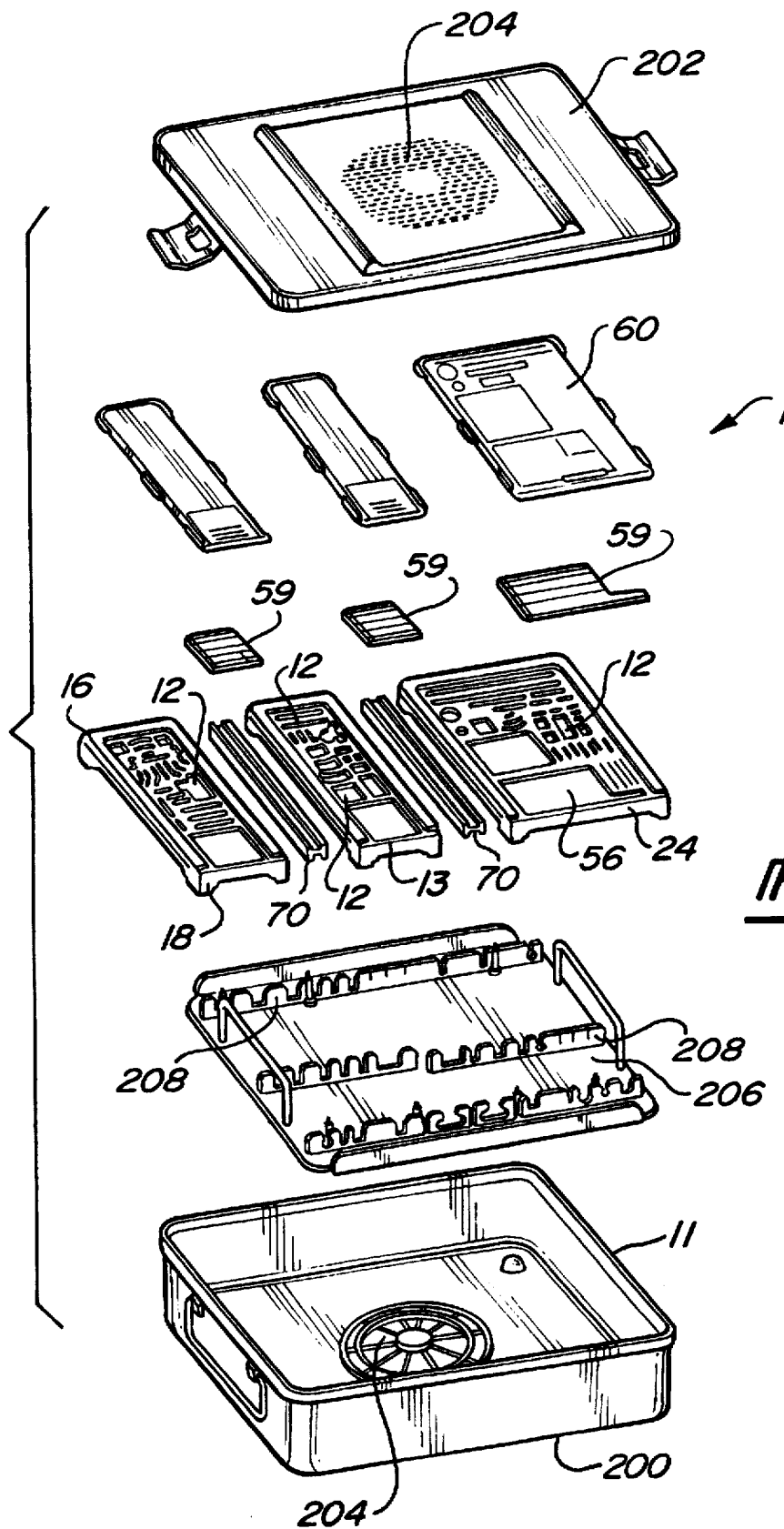
FIG. 1 is an exploded perspective view of the system for sterilizing implants of the present invention.

Referring to FIG. 1, a system for housing and sterilizing orthopedic devices for use in surgery is shown and is generally designated by the numeral 10. The system 10 is used for receiving orthopedic devices such as screws and plate systems, as well as various surgical instruments used to implant the screws and plate systems. The system 10 allows the orthopedic devices and instruments to be sterilized in a single sterilization case and then opened for use during a surgical procedure. It will also be understood that the system 10 does not necessarily have to involve the use of orthopedic devices, but may also be used to sterilize and store other devices as well.

The system 10 will now be described in greater detail. The system 10 includes a sterilization case 11 which includes a base member 200 and a cover member 202. The base member 200 and the cover member 202 each include filtered apertures 204 which allow for autoclave steam to enter the system 10 during the sterilization procedure as well as to allow for moisture drainage when the sterilization procedure has been completed. The system 10 also includes an instrument rack 206 which is used to receive the instruments (not shown) which are to be used in the surgical procedure. The instrument rack 206 includes a plurality of projections 208 which allow the instruments to be relatively positionally secured with respect to the instrument rack 206. In addition, the instrument rack 206 may also have a graphical image disposed thereon of the various instruments which are to be stored on the instrument rack 206 to allow the instruments to be more easily positioned on the instrument rack 206 during usage.

To provide means for storing and identifying different sets of orthopedic devices, the system 10 also includes a first container 13, a second container 18, and a third container 24. The containers 13, 18 and 24 are used for storing different sets of orthopedic devices within the sterilization case 11 during the sterilization procedure. For example, the container 13 may be used to store a dimensionally small (i.e., 1.0 mm) plate system for use in maxillofacial surgery, while the container 18 may be used to store a dimensionally larger (i.e., 1.5 mm) or different plate system also used in maxillofacial surgery. Finally, the container 24 may be used to store a still larger or different plate system for use in maxillofacial surgery. While the system 10 contains three containers, it will be appreciated that the system 10 may also have greater or fewer numbers of containers.

The containers 13, 18 and 24 include graphical indicia of the various orthopedic devices which are stored in the containers 13, 18 and 24. As will be more fully described below, the graphical indicia located on the containers 13, 18 and 24 permit identification of which particular orthopedic device is stored in which particular position within the first, second and third container 13, 18 and 24. In addition, the graphical indicia on the containers 13, 18 and 24 correspond to an inventory control sheet which facilitates inventory control in a manner more fully discussed below. The containers 13, 18 and 24 are preferably manufactured of polytetrafluoroethylene (PTFE). However, the containers 13, 18 and 24 may also be manufactured of aluminum or other suitable material that is capable of maintaining shape and resisting corrosion in the steam autoclave environment.

To provide means for removably securing the containers 13, 18 and 24 together, the system 10 further includes a plurality of connectors 70. As will be more fully described below, the connectors 70 allow different combination of the containers 13, 18 and 24 to be secured together for use by one particular surgeon, while allowing a different combination of the containers 13, 18 and 24 to be secured together for use by a different surgeon. The ability of the system 10 to removably secure several containers together provides several advantages. First, the surgeon is not required to have an individualized container made for the surgeon's specific usage. Rather, the surgeon is able to form a semi-custom container by selecting the individual containers and joining them together as desired. In addition, because several surgeons are able to join individual containers together as desired, the inventory of orthopedic devices needed to be maintained is reduced. This is because several surgeons are able to share the same container having a relatively small inventory of a certain specific type of orthopedic devices, instead of having several surgeons each with a separate custom-made container containing a duplicate inventory of the same devices.

The first container 13 will now be described in greater detail. As shown in FIG. 2a, the first container 13 includes a single pocket 56 with a series of holes 58 used for storage of screws. A plate 59 is inserted into the pocket 56 for use in identifying the screws placed into the holes 58. The plate is engraved with a size designation for the diameter and length of the screws. The corners 16 of the container 13 are rounded to enable the container 13 to be wrapped using current sterilization storage techniques if the sterilization case 11 is not used. A series of holes 28 through the entire container 13 are present for infiltration of autoclave steam and moisture drainage. A slot 54 is shown along the perimeter for engaging a lid 60. Cutout portions 52 of the slot allow for a shortened stroke in removing the lid 60 from the container 13.

Referring now to FIG. 2b, a side view of first container 13 is shown. A T-slot 30 is shown along the side 32 of the container. The T-slot 30 is used to connect the container 13 to the second container 18 as will be more fully discussed below. A leg 34 is shown extending from the base 36 of the container 13. In the shown embodiment, the leg 34 is integral with the container 13; however, it could be made as a separate piece. The leg 34 provides clearance for sterilization when the container 13 is placed into the sterilization case 11 as well as providing rigidity to the container 13. FIG. 2c shows an end view of the container 13 and gives another view of the legs 34 extending from the base 36.

Figure 2D:
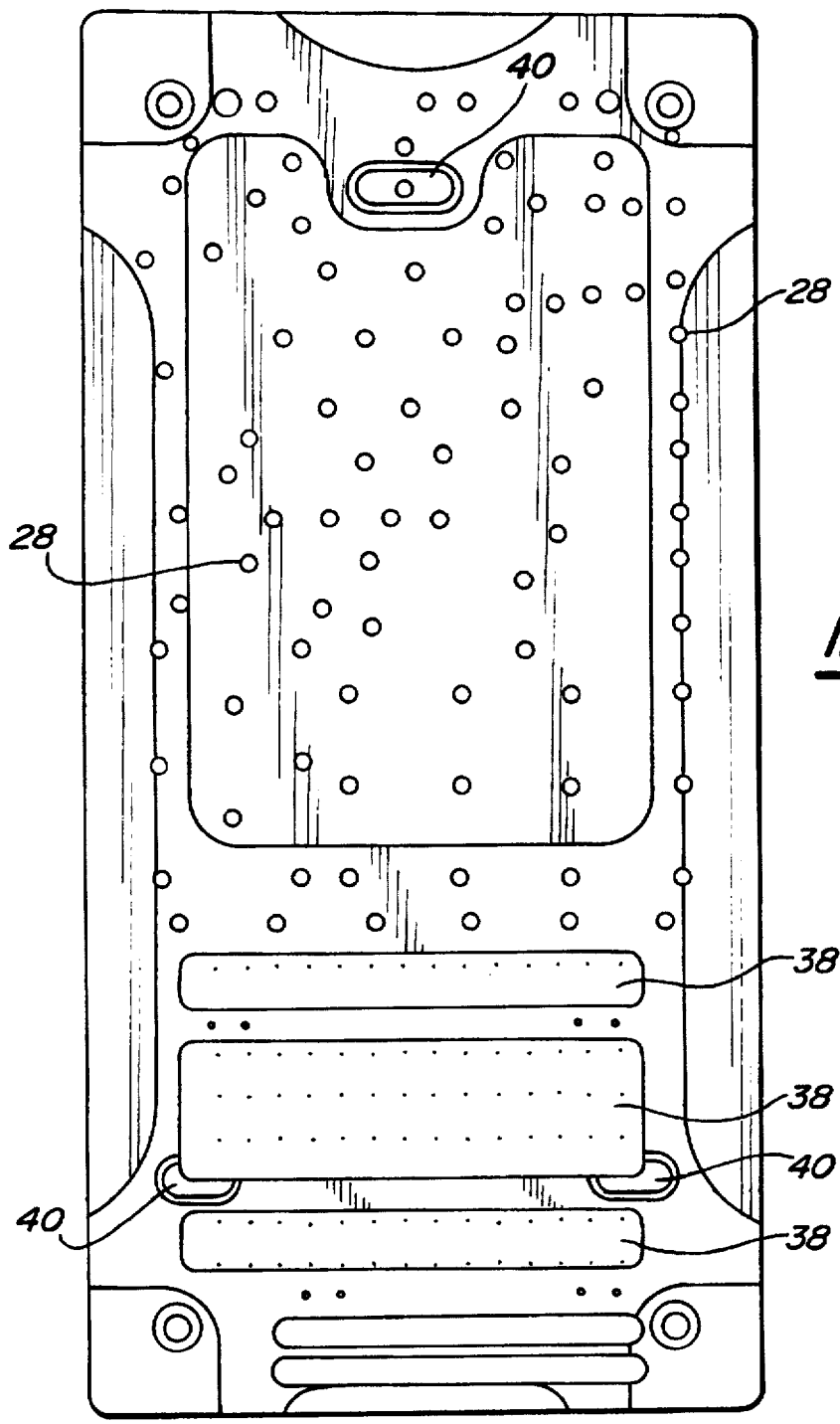
FIG. 2d is a bottom view of the first sterilization container of the present invention.
Figure 2C:
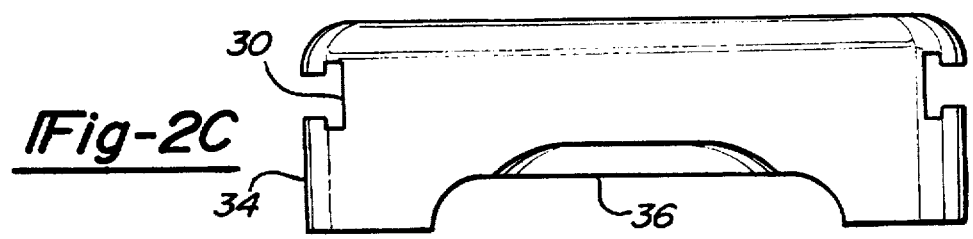
FIG. 2c is an end elevational view of the first sterilization container of the present invention.

Referring now to FIG. 2d, the bottom view of container 13 is shown. Slots 38 are present on the base of the container 13 for a quick reference check of proper placement of the screws in the container 13. The slots 38 are at varying depths to correspond to different lengths of screws used in the set. For example, if a 10 mm length screw is placed in a slot 38 intended to house a 5 mm screw, the 10 mm screw will extend past the slot by 5 mm letting the person loading or checking the contents of the container 13 know that the screw is in the wrong location. Also shown are recessed areas 40 used for resting the container 13 on top of the instrument rack 206 when container 13 is placed inside of the sterilization case 11. While the container 13 is normally used inside the larger sterilization case 11 during autoclaving and storage, it may also be used as a stand alone sterilization and storage container.

Figure 3D:
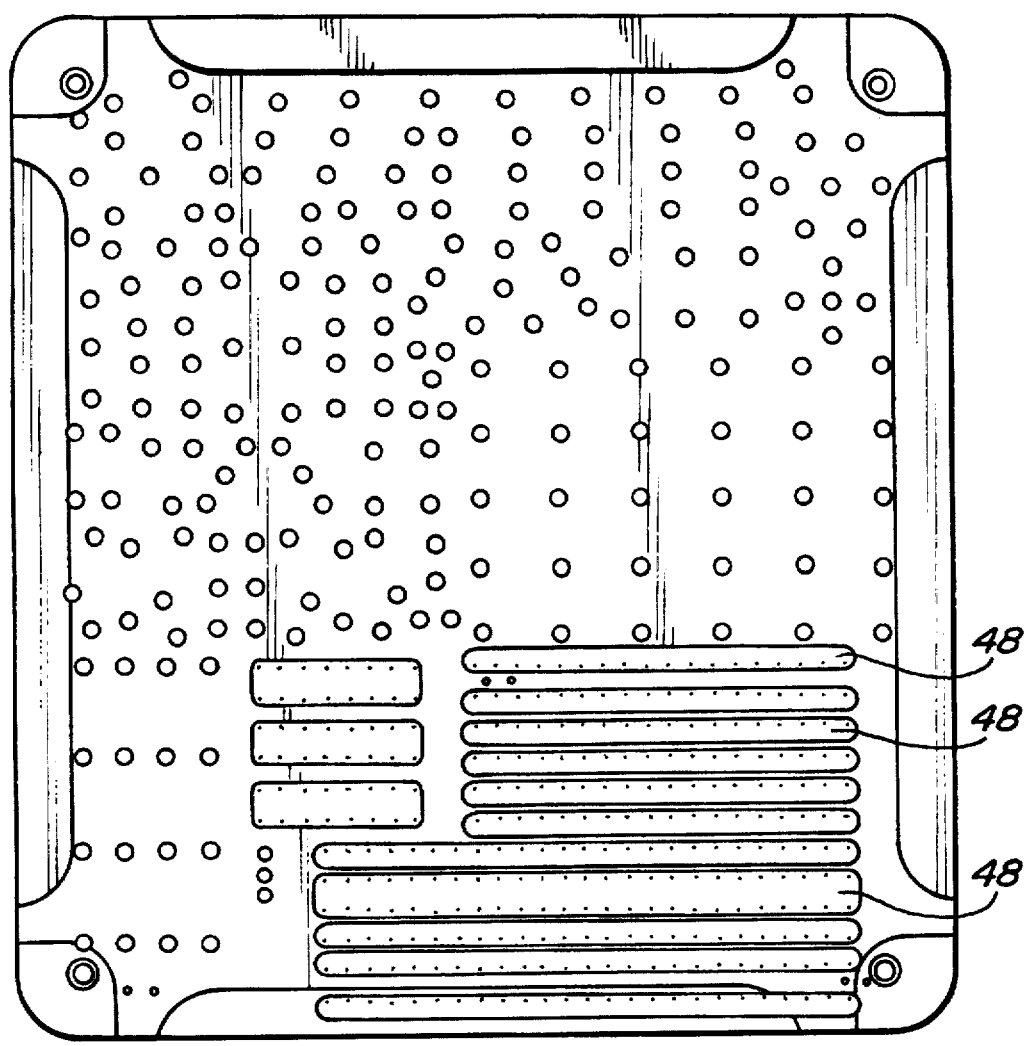
FIG. 3d is a bottom view of the second sterilization container of the present invention.
Figure 3C:
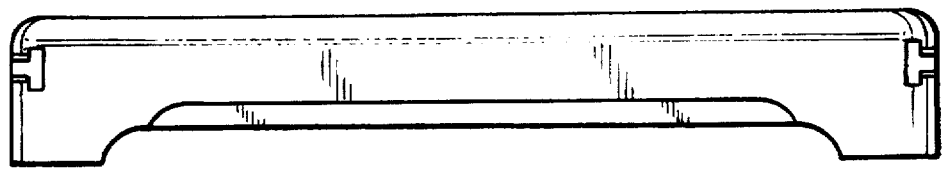
FIG. 3c is an end elevational view of the second sterilization container of the present invention.

Referring now to FIG. 3a, a second container 18 which may be of a different size is shown. The container 18 is also of a generally rectangular shape and contains different sized compartments 20 for housing a second set of orthopedic devices such as a 1.5 mm screw and plate system (not shown). The container 18 shown in FIGS. 3a through 3d has very similar features as described previously in FIG. 2, except it is designed to hold a different set of implants. In this regard, FIGS. 3b through 3d show similar features as FIGS. 2b through 2d such as base 42, side 44, legs 46, slots 48 and recessed areas 50.

FIG. 3e is an end view isolated on the T-slot 30 while FIG. 3f is a detail view of the side of the T-slot 30. A tight manufacturing tolerance on the width and depth of the T-slot 30 is preferred to aid in the stability of the junction between different containers such as item 13 and item 18. The depth of the slot 30 on the preferred embodiment is 0.254 inches with a tolerance of +0.005 inches and −0.002 inches. The dimension of the crossing portion of the T-slot 30 is 0.115 inches with a tolerance of ±0.002 inches. The width of the narrow portion is 0.128 inches with a tolerance of ±0.002 inches. The width of the widest portion of T-slot 30 is 0.375 inches with a tolerance of ±0.002 inches. The T-slot 30 includes a larger entry 62 for easier insertion of the connecting member 70. In addition, the T-slot 30 has a reduced section 64 a short distance in from the larger entry 62 as well as a second increased section 66 located just past the reduced section 64. The remaining portion 68 of the T-slot 30 is at the dimension for the desired stability as described above. The function of the reduced section 64 and the second increased section 66 is to act as a stop or resistance when the I-beam connector 70 is inserted into the T-slot 30 as will be discussed below.

Figure 4:
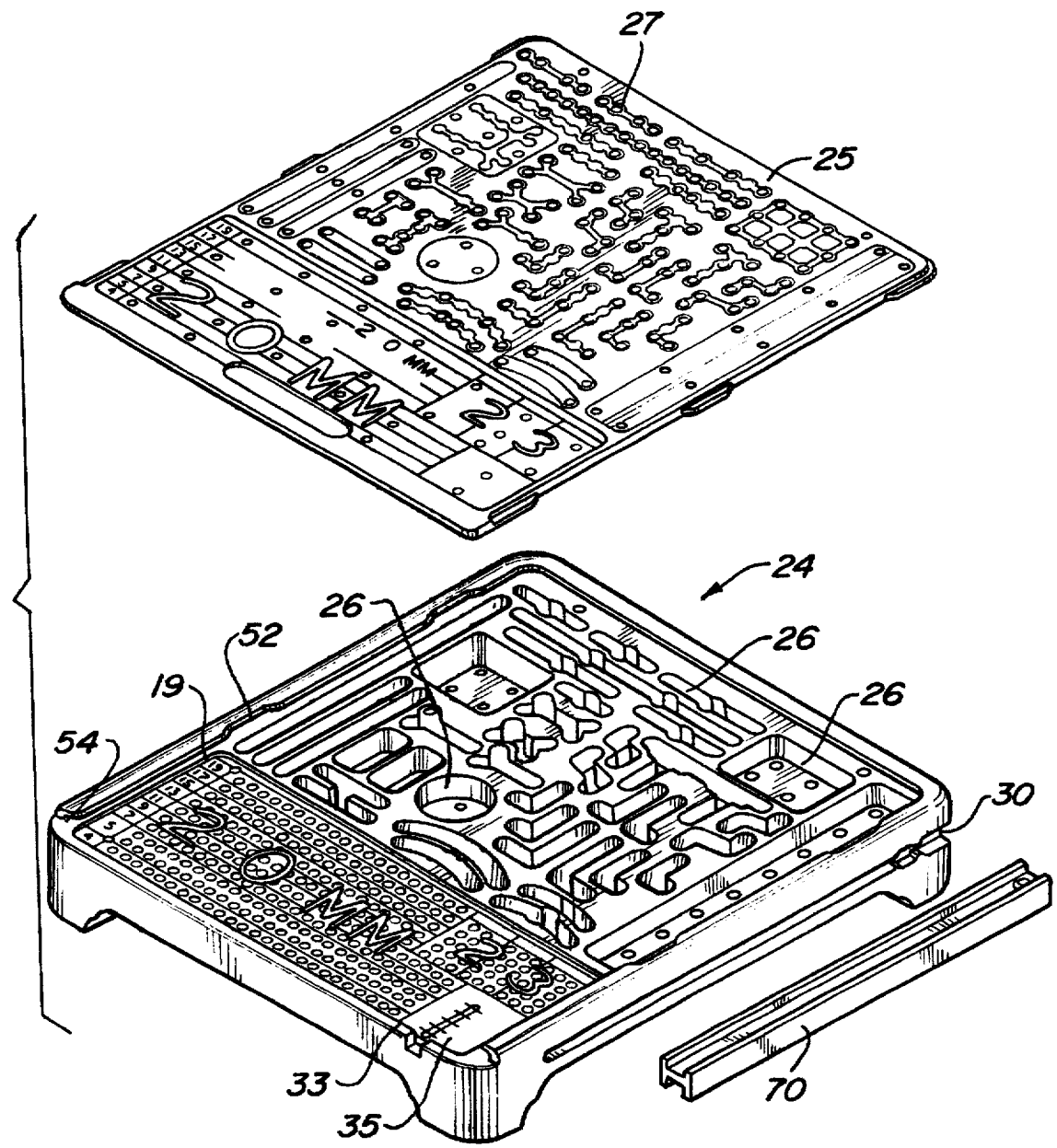
FIG. 4 is an exploded perspective view of a third sterilization container of the present invention.

Referring now to FIG. 4, a third container 24 is shown having different sized compartments 26 for housing yet another set of plates and screws. The features of the third container 24 are similar to those described earlier except the container 24 once again is designed to hold yet another set of implants. The third container 24 is shown with a lid 25 and connecting member 70. The lid 25 is made of aluminum; however, the lid could be made of any suitable material that is able to meet the environmental requirements of heat and corrosion resistance. The lid 25 is shown with indicia 27 matching the parts that will be held in the compartments 26. The third container 24 is shown with a plate 33 placed at one end of the container where implantable bone screws are stored. The plate 33 allows indicia to be placed on this portion to identify the length of the screws housed therein. A reference scale 35 is also present to help identify the screws as they are placed into the container.

Figure 5:
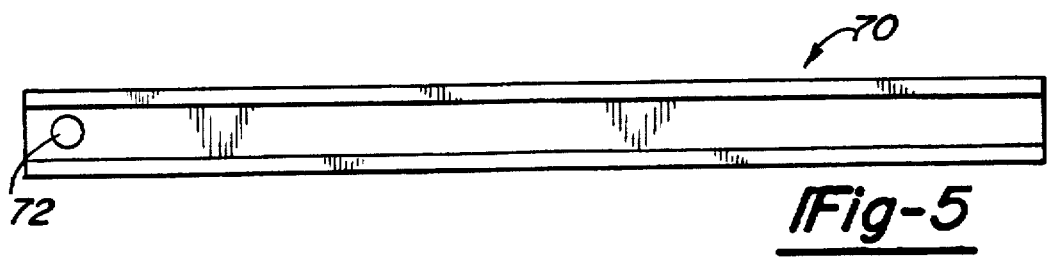
FIG. 5 is a top elevational view of the I-beam connector of the present invention.
Figure 6:
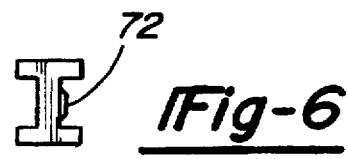
FIG. 6 is an end elevational view of the I-beam connector of the present invention.

To provide means or detachably mounting the first container 13 to the second container 18, the system 10 further includes an I-beam connector 70 as shown in FIG. 5. The I-beam connector 70 is roughly the same length as the T-slot 30 in the containers 13, 18 and 24 so as to provide as much stability as possible. The I-beam connector 70 has a small projection 72 protruding from the middle portion of the I-beam connector 70. The projection 72 communicates with the reduced section 64 on the second container 18 to help resist pull-out or disassociation of the I-beam connector 70 from the second container 18.

Figure 7:
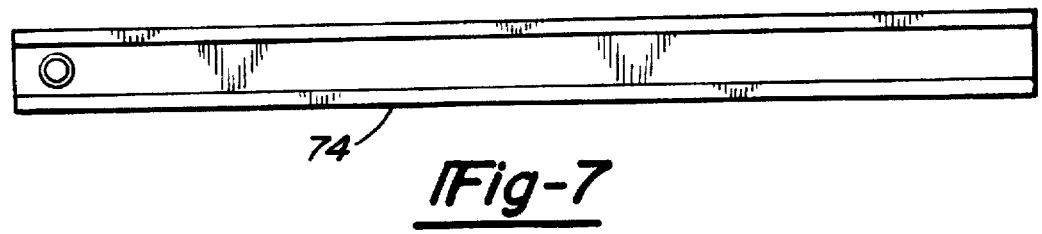
FIG. 7 is a top elevation view showing the bow of the I-beam connector of the present invention.

The I-beam connector 70 includes a slight bow 74 as shown in FIG. 7. The function of the slight bow 74 is to provide tension between the two containers that are joined together by the I-beam connector 70 so as to inhibit removal of the I-beam connector 70 from the T-slot 30. The radius of the bow 74 is 150 inches; however, any large radius could be used to accomplish the function. The I-beam connector 70 is made of a standard aluminum extrusion; however, it could be made of any number of materials that have the strength and corrosion resistance necessary as well as the cost effectiveness of manufacturing. While the I-beam connector 70 is shown to include the bow 74, other suitable interference structures may be used.

Figure 8:
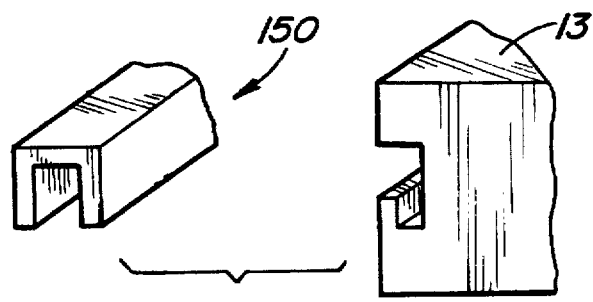
FIG. 8 is an end view of an alternative embodiment of the connector according to the present invention.
Figure 9:
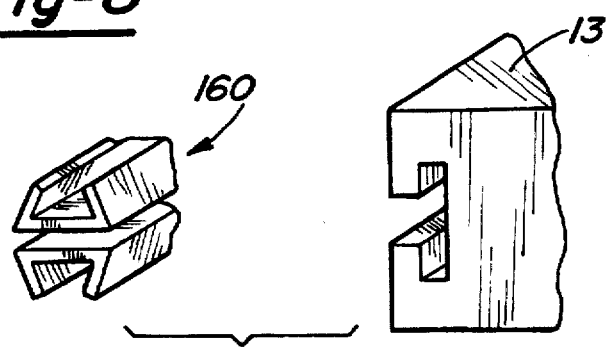
FIG. 9 is an end view of a third alternative embodiment of the connector according to the present invention.
Figure 10:
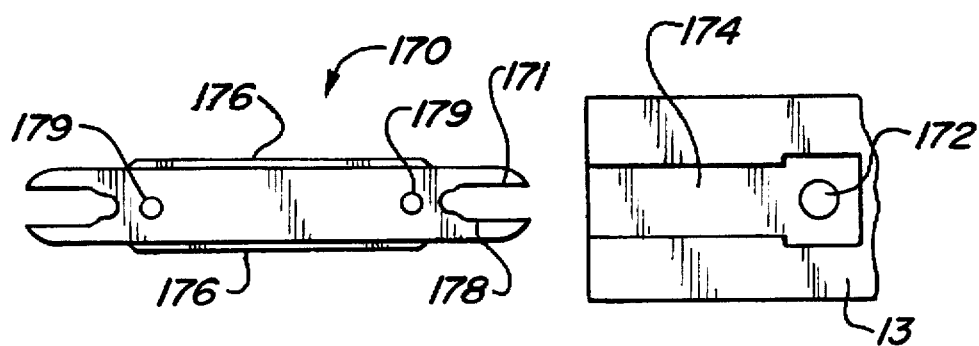
FIG. 10 is an end view of a fourth alternative embodiment of the connector according to the present invention.
Figure 11:
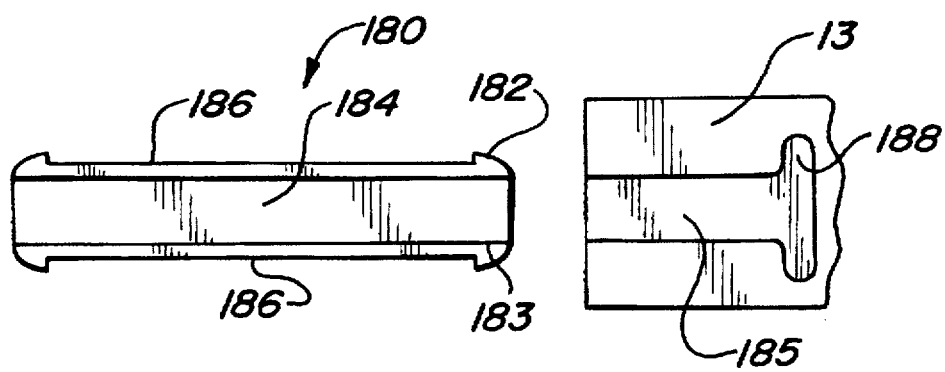
FIG. 11 is an end view of a fifth alternative embodiment of the connector according to the present invention.
Figure 12:
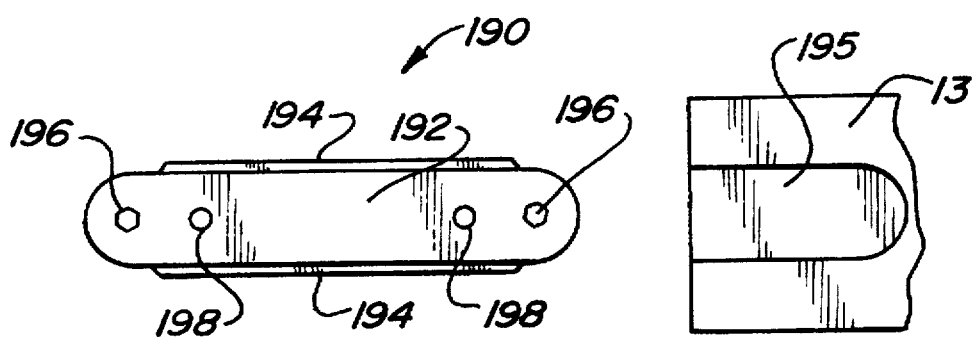
FIG. 12 is an end view of a sixth alternative embodiment of the connector according to the present invention.

FIGS. 8 through 12 are alternative embodiments of connectors and features that could be used to connect two containers such as first container 13 and second container 18 together. The corner of one container is shown along with a separate connector element. The connector 150 shown in FIG. 8 is a U-shaped channel and functions similar to I-beam connector 70. The connector element 160 shown in FIG. 9 is a pair of standard beveled channels that are placed back-to-back and inserted into a T-slot 30 in the container 13. Both the U-shaped channel connector 150 and the beveled channels 160 would have a bow similar to the I-beam connector 70. The connector element 170 shown in FIG. 10 includes at each end a straight portion 171 that flexes to extend over the pin 172 protruding from the container 13. The groove 174 in the container 13 is undercut at the edges to allow the blades 176 on both sides of the connector 170 to slide into the groove 174. The connector 170 has a hole 178 at the end of the straight portion 171 to allow the straight portion to return to its original shape. The two holes 179 were used for fixturing. The connector element 180 shown in FIG. 11 features a tang 182 on each end that is slit 183 along the main body 184 of the connector element 180 allowing the tang to flex as the connector element 180 is inserted into the container 13. The recessed area 188 at the end of the groove 185 allows the tang 182 to return to its normal state. The connector element 190 shown in FIG. 12 has a main body 192 and a set of blades 194 on both sides. The blades 194 slide into an undercut on groove 195 in the container 13. The connector element 190 is attached to the container 13 using the set-screws 196. Holes 198 are used for fixturing.

Figure 13:
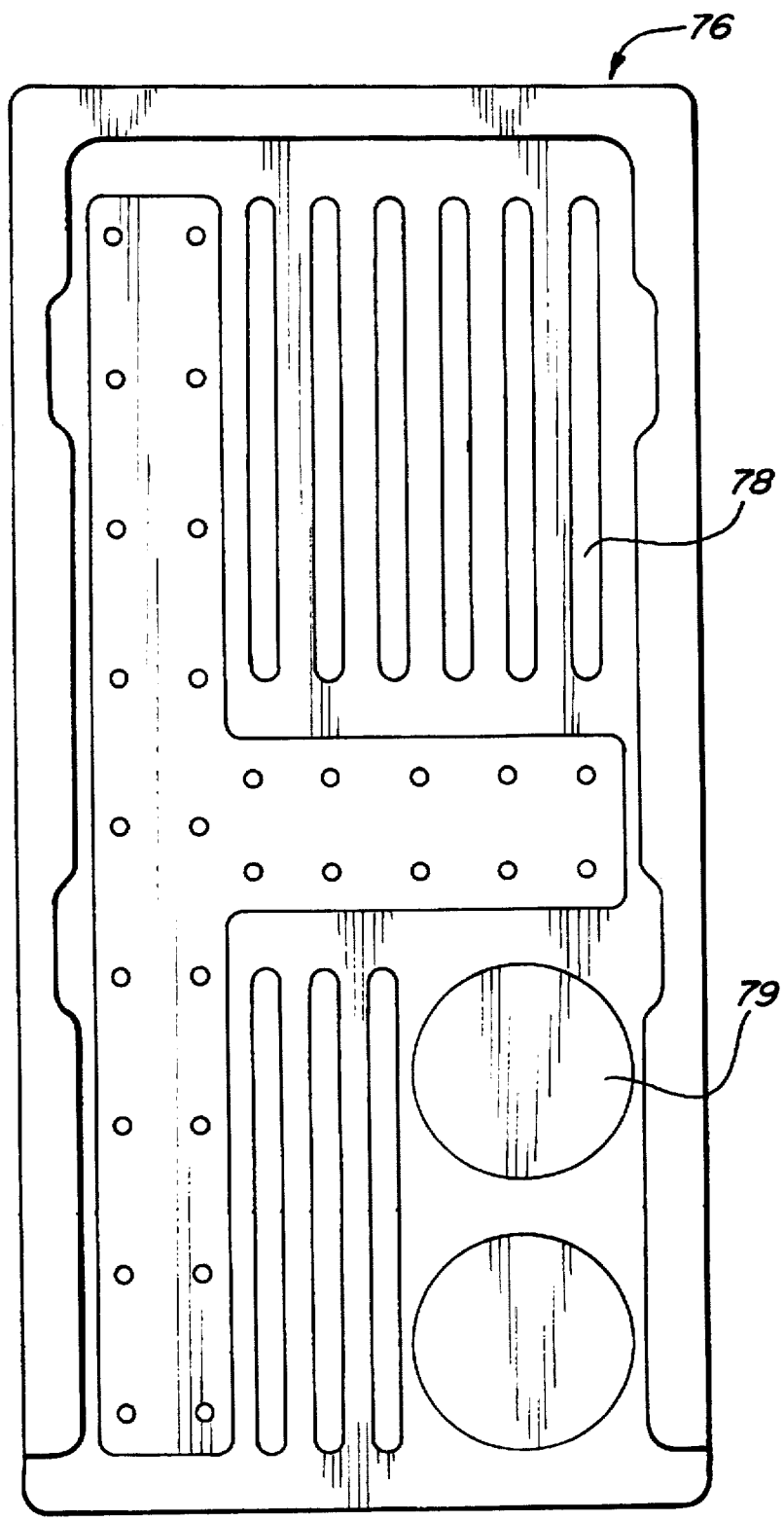
FIG. 13 is a top elevational view of a fourth sterilization container of the present invention.
Figure 18:
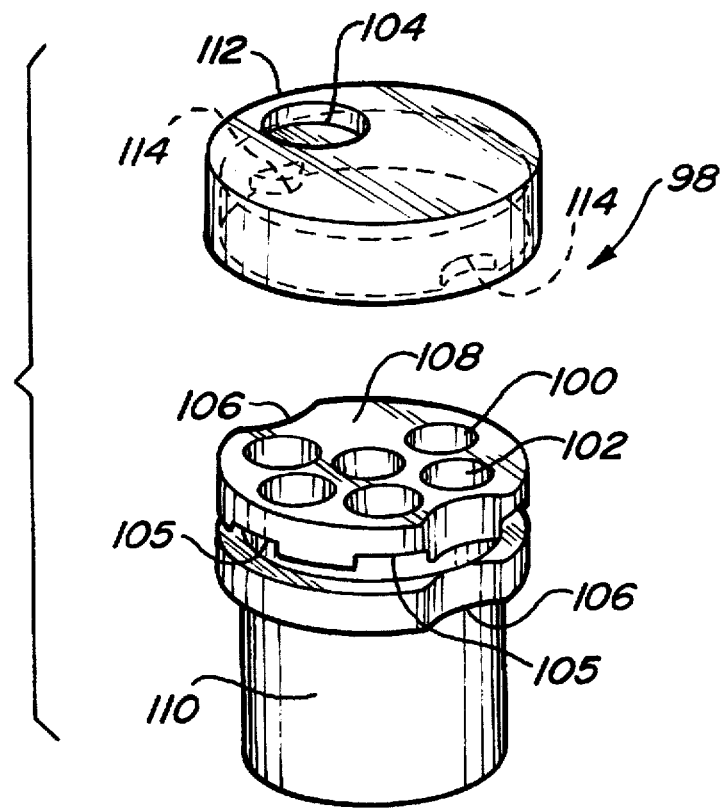
FIG. 18 is a perspective view of a second embodiment of the modular compartment of the present invention.

The present invention may also be used to store plates and screws which are themselves stored within a separate modular compartment. Using a modular compartment allows the devices to be shipped in a sterile environment and then be inserted into the larger storage container such as fourth container 76 shown in FIG. 13. The fourth container 76 has a series of apertures 78 and 79. The apertures 78 are of a predetermined size to be used in conjunction with modular compartments 80 or 98 shown in FIGS. 14 and 18. In this regard, the modular compartment 80 is designed to fit into the aperture 78 of the fourth container 76. The modular compartment 80 is manufactured of polycarbonate or other suitable material that can maintain its dimensional stability and integrity at autoclave temperatures. The particular shape shown in the drawing is somewhat rectangular; however, as will be demonstrated later, any geometric shape could be used. The external features of the fourth container 76 are similar to the container 13 shown in FIG. 2. A connector may be used to connect the fourth container 76 to another container 13, 18, 26 or 76. As shown in FIG. 15, the modular compartment 80 includes a slot 82 just below the upper surface 84. The slot 82 includes a series of indentations 88 as shown in FIG. 16. The slot 82 is used as a sliding track for a lid 86 to engage while the indentations 88 on the slot 82 are used to allow the lid 86 to advance in an incremental manner. A series of holes 81 are present in the modular compartment 80 for storage of implantable screws (not shown). While the modular compartment 80 is shown with ten (10) holes 81, the compartment 80 could be made with any number of holes that would be practical.

The lid 86 will now be described in greater detail with reference to FIG. 17. In this regard, the lid 86 is shown with a T-shaped slot 89. One end of the T-shaped slot 89 is open 90 while the other end is closed 92. At the open end of slot 89 is a projection 94 that emerges from the slot 89. The dimension of the projection 94 is such that the projection 94 cooperates with the indentations 88 on the container 76 to allow for incremental opening of the lid 86 relative to the container 76. The outer surface of the lid 86 has a raised portion 96 to allow for manipulation of the lid 86 to remove the implants that may be located within the compartment 80. The closed end 92 of the T-shaped slot 88 functions as a stop when the lid 86 slides onto the modular compartment 80. The compartment 98 shown in FIG. 18 has a series of holes 100 running parallel to the cylindrical section. The compartment 98 has five holes although it is possible to place more or less holes in the compartment. The holes are counterbored 102 at one end to allow the implantable screws (not shown) housed inside to seat below the proximal end 108 of the modular compartment 98. A pair of cutouts 106 on the proximal end 108 of the body portion 110 of the modular compartment 98 are used to allow the tabs 114 to clear the body portion 110 and thereby allow lid 112 to seat on the proximal end 108. The cutouts 105 on the bottom side of the proximal portion are used in conjunction with the tabs 114 on the lid to allow for incremental movement of the lid thereby allowing singular removal of the components housed inside. A spring could be used in the center of the body to keep the tabs biased against the cutouts 105. An alternative to this is to simply have a slightly raised dimple in the center of the body that the lid 112 must bend against to fit over the proximal end 108. The lid 112 must then be flexible to allow for the biasing of the lid in relation to the body 110. The lid 112 has two tabs 114 on the underside that cooperate with the cutouts 106 on the body portion 110. A hole 104 through the lid 112 allows for access to the screws housed inside.

While the two embodiments of the modular compartments 80 and 98 shown are for housing implantable bone screws, the invention could also be used to house bone plates and instruments.

Figure 19:
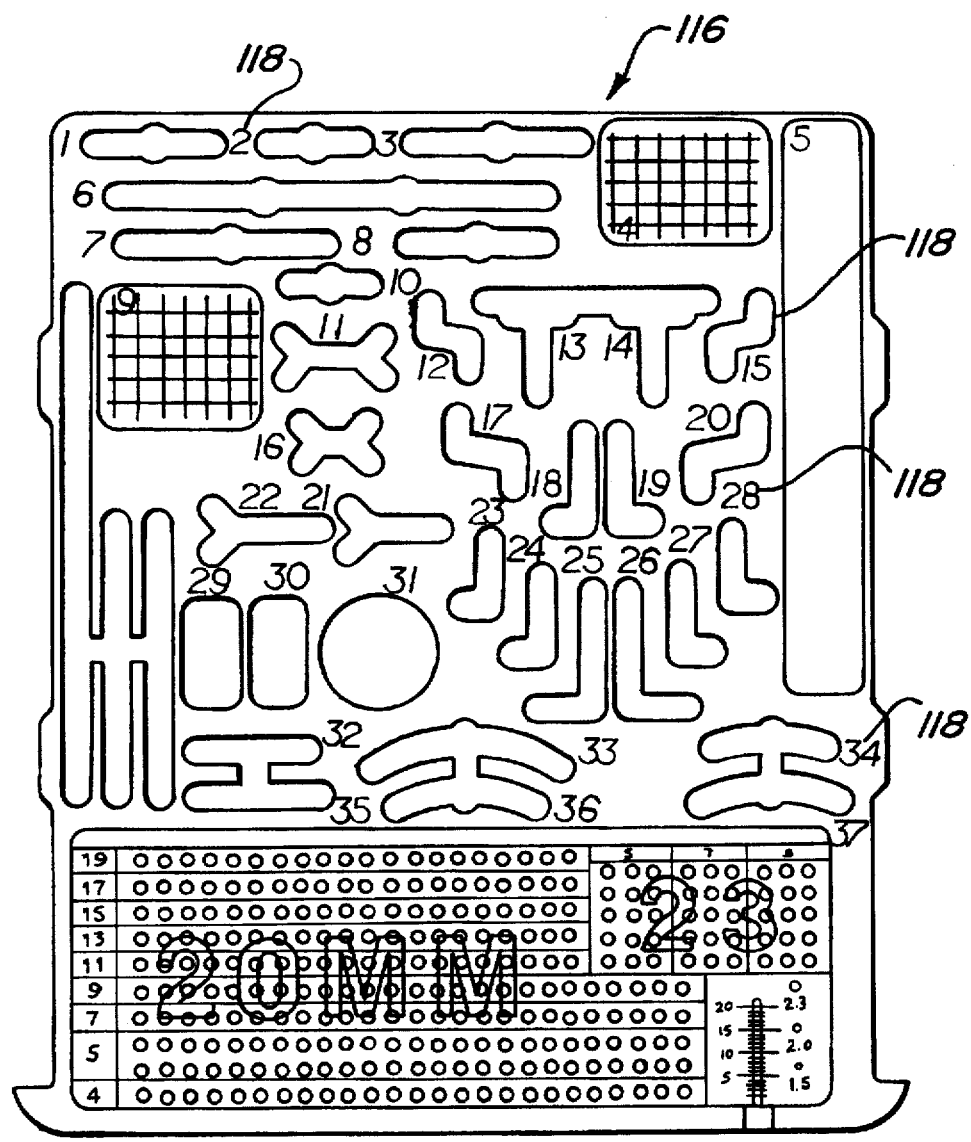
FIG. 19 is a top elevational view of the lid of the sterilization container of the present invention.
Figure 20:
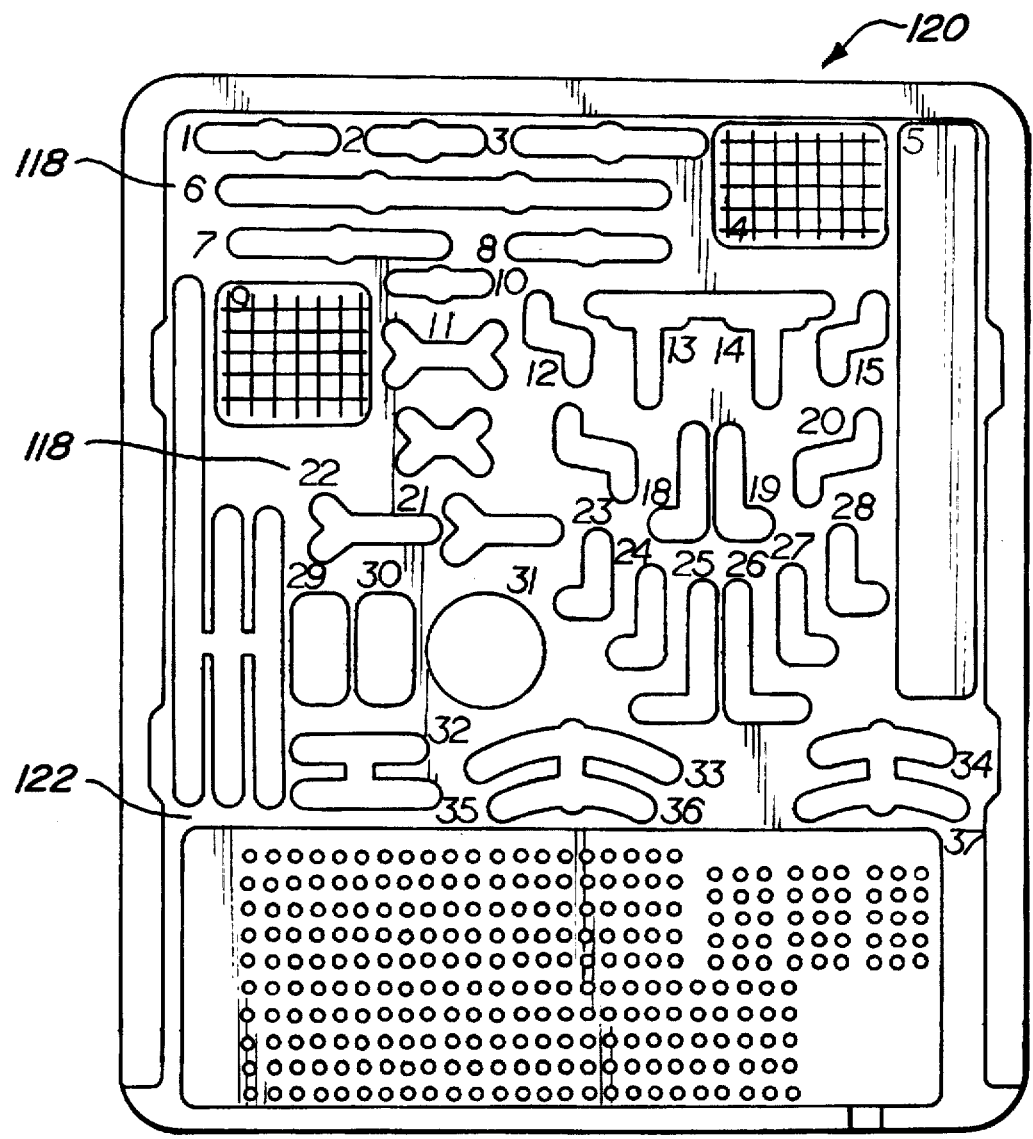
FIG. 20 is a top view of the inventory control sheet of the present invention.

The present invention also allows for inventory control with respect to implants and screws used with the system 10. In this regard, the lid 116 with generic marking 118 shown in FIG. 19 corresponds to the layout of the compartments of the container 13 as well as the layout of an inventory control sheet 120. Each inventory control sheet 120 provided corresponds to a specific container. The marking on the inventory control sheet 120 could also contain space for the manufacturing lot number and the manufacturer's part number.

The method of controlling the inventory using the lid 116 and the inventory control sheet 120 will now be described. In this regard, the hospital is provided with an original set of orthopedic devices to be placed in the compartments 12 that are in the containers 13, 18, 26, 76 or any combination of these as well as a lid 116 with a generic marking or identification code 118. An inventory control sheet 120 is also provided with a layout that duplicates the generic coding on the lid 116. The inventory control sheet 120 is then customized by the hospital to identify the implants in each compartment 12. The front side 122 of the inventory control sheet 120 matches the layout of the compartments 12 in container 13, while the reverse side 124 of the inventory control sheet 120 has a marking identification 126 that also corresponds to the generic marking 118 on the front side 122 and the lid 116. The reverse side 124 is used to identify all orthopedic devices placed into the compartments 12 by part number and manufacturing lot number. A preprinted set of labels are supplied to the hospital as well. The labels contain graphics of the implants supplied and the manufacturing part number. These labels are attached to the front side 122 of the inventory control sheet 120 by hospital personnel. A second set of labels containing the part number and item description are supplied for placing on the reverse side 124 of the inventory control sheet 120. In this way, the inventory control sheet 120 is customized by the hospital as the implants are loaded into the container 13. When the orthopedic devices are restocked after surgery, the inventory control sheet 120 is updated with the new part numbers and lot numbers where necessary. The lid 116 is marked using a methylene blue or alcohol pen in the sterile field as the components are removed or used in the surgery. The marks from the lid 116 are transferred to the inventory control sheet 120 after surgery. The inventory control sheet 120 is then used to transfer the orthopedic devices from hospital inventory to the patient bill. The above process is repeated for each succeeding surgery thereby maintaining accurate inventory control and passing the cost of each implant to the particular patient for which it was used in. When a new orthopedic device is placed in the set, the only change necessary is to update the front side 122 and the reverse side 124 of the inventory control sheet 120.

Alternatives to this method would be to place a removable label onto the inventory control sheet 120. The label would have the part number, description and manufacturing lot number printed on it. The information could be of a machine readable format as well. When an orthopedic device is used in surgery, a label could be removed from the inventory control sheet 120 and placed onto the patient's chart for the direct billing and inventory control concerns.

A series of removable labels could also be placed onto the modular compartments 80 and 98. When an item is removed from the compartment 80 or 98, a label could be removed from the compartment 80 or 98 and placed onto the patient's chart. The label may have to be sterilizable in an autoclave environment as well as a gamma ray irradiation sterilization environment.

The modular compartments 80 or 98 could also have the manufacturing part number and lot number placed directly on the compartment. The advantage of this is that if a part number changes or a different orthopedic device is placed in the container, the surgical staff will have an easy method to record the part number and lot number to maintain the hospital inventory and properly record patient charges.

It will be appreciated that the foregoing description of the various embodiments of the invention is presented by way of illustration only and not by way of any limitation, and that various alternatives and modifications may be made to the illustrated embodiments without departing from the spirit and scope of the invention.

What is claimed is:

1. A system for housing and sterilizing medical devices for use in surgery, comprising:

a first container having a first geometric shape and a first plurality of various size compartments, said first plurality of various size compartments operable to store a first set of medical devices and said first container including a first plurality of apertures operable to permit said first set of medical devices to be sterilized; and a second container having a second geometric shape and a second plurality of various size compartments, said second plurality of various size compartments operable to store a second set of medical devices and said second container including a second plurality of apertures operable to permit said second set of medical devices to be sterilized, wherein said second container is detachably mounted adjacent to said first container.

2. The system of claim 1, wherein said first container is detachably mounted to said second container with a bowed connector having an I-beam shaped cross-section.

3. The system of claim 2, wherein said first container and second container each have a side wall with a T-shaped slot formed therein for axially receiving said bowed connector having said I-beam shaped cross-section.

4. The system of claim 1, wherein at least one of said first plurality of various size compartments is removable from said first container.

5. The system of claim 4, wherein an identification label is attached to said at least one removable compartment.

6. The system of claim 1, wherein said first container is detachably mounted to said second container with a bowed connector having a channel-shaped cross-section.

7. The system of claim 1, wherein said first container is detachably mounted to said second container with a bowed connector having an opposing pair of beveled channels.

8. The system of claim 1, further comprising said first set of medical devices operable to be stored by said first container and said second set of medical devices operable to be stored by said second container.

9. A system for sterilizing and housing medical devices, comprising:

a first container defining a first plurality of apertures, each of said first plurality of apertures having a predetermined size;

a first set of sterilized medical devices; and at least one modular compartment sized to fit within at least one of said first plurality of apertures, said at least one modular compartment storing said first set of sterilized medical devices in a sterilized environment, wherein said at least one modular compartment is removably positioned within one of said first plurality of apertures in said container.

10. The system of claim 9, wherein said at least one modular compartment includes an identification label bearing a manufacturing part number and a lot number to maintain inventory control.

11. The system of claim 9, wherein said at least one modular compartment includes a first plurality of holes for storing said first set of sterilized medical devices.

12. The system of claim 11, wherein said at least one modular compartment further includes a lid that seals said at least one modular compartment to prevent removal of said first set of sterilized medical devices.

13. The system of claim 12, wherein said lid communicates with said at least one modular compartment to allow incremental removal of said lid.

14. The system of claim 11, wherein said at least one modular compartment is cylindrical in shape.

15. The system of claim 9, further comprising a second container storing a second set of sterilized medical devices, said second container detachably mounted adjacent to said first container.

16. A system for sterilizing and housing at least a first set of medical devices and a second set of medical devices, said system comprising:

a sterilization case having a base member and a cover member with a first plurality of apertures passing therethrough;

a first container stored in said sterilization case having a second plurality of apertures, said first container operable to store said first set of medical devices;

a second container stored in said sterilization case having a third plurality of apertures, said second container operable to store said second set of medical devices; and a connector operable to detachably connect said first container adjacent to said second container, wherein said first, second and third plurality of apertures are operable to permit said first and second set of medical devices to be sterilized.

17. The system of claim 16, wherein said connector is a bowed connector having an I-beam shaped cross-section.

18. The system of claim 17, wherein said first container and said second container each have a side wall with a T-shaped slot formed therein for axially receiving said bowed connector having said I-beam shaped cross-section.

19. The system of claim 16, wherein said first container includes a first plurality of various size compartments and said second container includes a second plurality of various size compartments.

20. The system of claim 19, wherein at least one of said first plurality of various size compartments is removable from said first container and at least one of said second plurality of various size compartments is removable from said second container.

21. The system of claim 18, wherein said at least one removable compartment from said first plurality of various size compartments stores said first set of medical devices and said at least one removable compartment from said second plurality of various size compartments stores said second set of medical devices.

22. The system of claim 16, further comprising said first set of medical devices and said second set of medical devices.

* * * * *